US007642291B2

(12) United States Patent
Jeong et al.

(10) Patent No.: US 7,642,291 B2
(45) Date of Patent: Jan. 5, 2010

(54) O-ACYLOXIME DERIVATIVES, PREPARATION METHOD THEREOF, AND PHARMACEUTICAL COMPOSITION CONTAINING THE SAME FOR PREVENTION AND TREATMENT OF CARDIOVASCULAR DISEASE

(75) Inventors: Tae-Sook Jeong, Daejeon (KR);
Woo-Song Lee, Daejeon (KR);
Hyung-Jae Jeong, Gyeongsangnam-do (KR); Yong-Dae Park, Daejeon (KR);
Jong-Min Han, Daejeon (KR);
Hyoung-Chin Kim, Daejeon (KR);
Og-Sung Moon, Daejeon (KR);
Young-Suk Won, Daejeon (KR)

(73) Assignee: Korea Research Institute of Bioscience and Biotechnology, Daejeon (KR)

( * ) Notice: Subject to any disclaimer, the term of this patent is extended or adjusted under 35 U.S.C. 154(b) by 631 days.

(21) Appl. No.: 11/163,383

(22) Filed: Oct. 17, 2005

(65) Prior Publication Data

US 2006/0106017 A1    May 18, 2006

(30) Foreign Application Priority Data

Nov. 12, 2004    (KR) .................. 10-2004-0092263

(51) Int. Cl.
*A61K 31/15* (2006.01)
*C07C 251/68* (2006.01)
(52) U.S. Cl. ...................... 514/640; 564/254
(58) Field of Classification Search ............... 514/640; 564/256
See application file for complete search history.

(56) References Cited

U.S. PATENT DOCUMENTS 3,503,732 A * 3/1970 Cahoy .................. 504/344
4,451,286 A * 5/1984 Martin .................. 504/110

OTHER PUBLICATIONS

Cho et al., Elimination Reactions of (E)- and (Z)-Benzaldehyde O-Benzoyloximes. Transition State Differences for the Syn- and Anti-Eliminations Forming Nitriles, 1998, J. Org. Chem., 63(14), pp. 4688 and 4689.*
Hill et al., Pyrolysis of benzoyl-.alpha.-benzaldoximes. I. Effect of substitution, solvents, and catalysts, 1967, J. Org. Chem., 32(12), p. 4025.*
Packard et al., "Lipoprotein-Associated Phospholipase A2 as an Independent Predictor of Coronary Heart Disease", New England Journal of Medicine (2000), 343: 1148-1155.
Dada et al., "Lp-PLA2: an emerging biomarker of coronary heart disease", Expert Rev. Mol. Diagn (2002), 2(1): 17-22.
Tew et al., "Purification, Properties, Sequencing, and Cloning of a Lipoprotein-Associated, Serine-Dependent Phospholipase Involved in the Oxidative Modification of Low-Density Lipoproteins", Arteriosclerosis, Thrombosis, and Vascular Biology (1996), 16(4): 591-595.
Tselepis et al., "PAF-Degrading Acetylhydrolase is Preferentially Associated with Dense LDL and VHDL-1 in Human Plasma", Arteriosclerosis, Thrombosis, and Vascular Biology (1995), 15: 1764-1773.
Macphee, et al., "Lipoprotein-associated phospholipase A2, platelet-activating factor acetylhydrolase, generates two bioactive products during the oxidation of low-density lipoprotein: use of a novel inhibitor", Biochem. J. (1999) 338: 479-487.
Macphee, Colin, "Lipoprotein-Associated Phospholipase A2, Platelet-Activating Factor Acetylhydrolase, is Expressed by Macrophages in Human and Rabbit Atherosclerotic Lesions", Arteriosclerosis, Thrombosis, and Vascular Biology (1999), 19: 2909-2971.
Häkkinen et al., "Lipoprotein-Associated Phospholipase A2, Platelet-Activating Factor Acetylhydrolase, Is Expressed by Macrophages in Human and Rabbit Atherosclerotic Lesions", Arteriosclerosis, Thrombosis, and Vascular Biology (1999), 19: 2909-2971.
Abstract, XIIth International Symposium on Atherosclerosis (2000), 151: 166.
Thirkettle et al., "SB-253514 and Analogues; Novel Inhibitors of Lipoprotein-Associated Phospholipase A2 Produced by Pseudomas fluorescens DSM 11579", The Journal of Antibiotics (2000), 53(7): 664-669.
Boyd et al., "N-1 Substituted Pyrimidin-4-ones: Novel, Orally Active Inhibitors of Lipoprotein-Associated Phospholipase A2", Bioorganic & Medicinal Chemistry Letters (2000), 10: 2557-2561.
Jeong et al. Abstract, 94th National Meeting of the Korean Chemical Society (Oct. 21, 2004).

* cited by examiner

*Primary Examiner*—Kamal A Saeed
*Assistant Examiner*—Kristin Bianchi
(74) *Attorney, Agent, or Firm*—Lucas & Mercanti, LLP

(57) ABSTRACT

The present invention relates to novel O-acyloxime derivatives, a preparation method thereof and a pharmaceutical composition comprising the same for prevention and treatment of cardiovascular disease. The O-acyloxime derivatives according to the present invention may valuably be used for prevention and treatment of cardiovascular diseases such as hyperlipidemia, coronary arterial heart disease, atherosclerosis, and myocardial infarction caused by $Lp\text{-}PLA_2$, because they have excellent inhibitory effect of $Lp\text{-}PLA_2$.

7 Claims, No Drawings

O-ACYLOXIME DERIVATIVES, PREPARATION METHOD THEREOF, AND PHARMACEUTICAL COMPOSITION CONTAINING THE SAME FOR PREVENTION AND TREATMENT OF CARDIOVASCULAR DISEASE

BACKGROUND OF THE INVENTION

1. Field of the Invention

The present invention relates to novel O-acyloxime derivatives, a preparation method thereof and a pharmaceutical composition comprising the same for prevention and treatment of cardiovascular disease.

2. Description of the Prior Art

Recently, mortality from coronary heart disease (CHD) is significantly increased, and atherosclerosis is one of the major causes of death. Atherosclerosis is an inflammatory disease caused by accumulation of lipid and fibrin on the arterial wall, and the major causes of the disease are hypertension, smoking, obesity, increase of low-density lipoprotein (LDL) in plasma. However, another cause of the atherosclerosis may be inferred from the fact that more than 50% of patients have contracted atherosclerosis regardless of the above causes. According to the investigation result of 580 patients having coronary heart disease and 1,160 normal men, which is reported by the West of Scotland Coronary Prevention Study (WOSCOPS), lipoprotein-associated Phospholipase $A_2$ (Lp-$PLA_2$) levels of the patients were significantly high compared to that of the normal men (N. Engl. J. Med., 2000, 343, 1148-1155), and it has been identified that Lp-$PLA_2$ is an independent risk factor of coronary heart disease (Expert Rev. Mol. Diagn., 2002, 2, 17-22).

The molecular weight of Lp-$PLA_2$ is 45 kDa. Lp-$PLA_2$ is a secreted calcium-independent member type VII of phospholiphase $A_2$ superfamily mainly formed by monocyte, macrophage, T-lymphocytes, and mast cells, and is known as an enzyme of platelet-activating factor acetylhydrolase (PAF-AH, EC 3.1.1.47) (Arterioscler. Thromb. Vasc. Biol., 1996, 16, 591-595). Additionally, 80% of Lp-$PLA_2$ is bound to LDL, and the remainder is bound to high-density lipoprotein (HDL) and very low-density lipoprotein (VLDL) (Arterioscler. Thromb. Vasc. Biol, 1995, 75, 1764-1773).

Accumulation of LDL, particularly oxidized LDL, on the arterial wall is known as the most important initial step of atherosclerosis. Lp-$PLA_2$ is bound to LDL in a latent state until LDL is oxidized or modified. As LDL is oxidized, Lp-$PLA_2$ is activated and forms a large amount of lysophosphatidylcholine (lyso-PC) and free oxidized fatty acids by rapidly hydrolyzing the sn-2 fatty acid of oxidized phospholipid (Biochem. J., 1999, 338, 479-487). LDL is oxidized in intima and serves as a substrate of Lp-$PLA_2$. Hydrolyzed products further accelerate chronic inflammation related to accumulation of macrophage, and a positive feedback mechanism of macrophage forming a large amount of Lp-$PLA_2$ further accelerates progress of vascular disorder. Biological activity has not been defined completely yet, because structures of free oxidized fatty acids formed by Lp-$PLA_2$ are not clearly identified. Fatty acids of micromolar concentration formed from ox-LDL are biologically inactive. However, in 1990s, reports on pro-inflammatory and pro-atherogenic role of lyso-PC, which is another decomposed product, were rapidly increased. For example, the reported roles are impairment of endothelium-dependent relaxation, inducement of vascular cell and intracellular adhesion molecules, activity as chemoattractant of monocyte and T-lymphocytes, suppressed production and release of endothelium-derived nitric oxide, inhibition of macrophage migration, toxicity at the concentration higher than 30-50 micromole, and release stimulation of arachidonic acid from endothelial cells (Curr. Opin. Pharmacol., 2001, 7,121-125).

Lp-$PLA_2$ is an independent risk factor of coronary artery disease in the case of hypercholestrolemia patients, and is suggested as a pro-inflammatory agent, which is detected in macrophage of atherosclerotic lesions (Arterioscler. Thromb. Vasc. Biol., 1999, 19, 2909-2971). According to recent researches, the formation of fatty streak in Watanabe heritable hyperlipidemic rabbits, which is a model animal of atherosclerosis, is significantly decreased by dosing Lp-$PLA_2$ inhibitor (Atherosclerosis, 2000, 151, 166). Therefore, inhibition of Lp-$PLA_2$ activity is highlighted as a target for prevention and treatment of atherosclerosis (N. Engl. J. Med., 2000, 343,1148-55). Accordingly, research and development of Lp-$PLA_2$ inhibitor will be very important for prevention and treatment of atherosclerosis.

GlaxoSmithKline isolated a series of novel inhibitors of Lp-$PLA_2$ from the culture broths of Pseudomonas fluorescens (J. Antibiotics, 2000, 53, 664-669). A potent, orally active Lp-$PLA_2$ inhibitor, SB-480848, has been developed from their synthetic derivatives, and SB-480848 is currently in a phase II clinical study.

Through researches on novel drugs for treatment of hyperlipidemia and atherosclerosis, the inventors have synthesized O-acyloxime derivatives, and completed the present invention by identifying that these compounds have inhibitory effects on Lp-$PLA_2$.

SUMMARY OF THE INVENTION

The present invention provides novel O-acyloxime derivatives.

Additionally, the present invention provides a preparation method of the O-acyloxime derivatives.

Additionally, the present invention provides a pharmaceutical composition for prevention and treatment of cardiovascular disease, comprising the O-acyloxime derivatives as active ingredients.

DETAILED DESCRIPTION OF THE INVENTION

The present invention provides novel O-acyloxime derivatives represented by the following Formula 1:

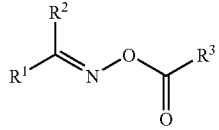

Formula 1

Wherein:

$R^1$ is aryl; heteroaryl such as furan, thiophene, imidazole, pyrrole, pyridine, pyrimidine and so on; aryl or heteroaryl substituted by one or more group selected from halogen, $C_1$~$C_6$ alkyl, $C_1$~$C_6$ alkoxy, $C_1$~$C_6$ alkylthio, cyano, amino, mono- or di-$C_1$~$C_6$ alkylamino, $C_2$~$C_6$ alkylcarbonyl, $C_1$~$C_6$ alkyl substituted by one or more halogen, aryl, $C_6$~$C_{10}$ arylalkyl, aryl or $C_6$~$C_{10}$ arylalkyl substituted by one or more halogen, and $C_6$~$C_{10}$ arylcarbonyl; $C_2$~$C_6$ heterocyclic ring comprising one or more N, O or S such as tetrahydrofuran, tetrahydropyran, piperidine, morpholine, thiomorpholine and so on; arylalkenyl;

R² is hydrogen; halogen; C₁~C₆ alkyl; hydroxy; amino; cyano; C₁~C₆ alkylamino; di(C₁~C₆ alkyl)amino; (C₁~C₃) alkylcarbonylamino; di(C₁~C₃ alkylcarbonyl)amino; C₁~C₆ alkoxy; aryl(C₁~C₃)alkoxy; heteroaryl such as pyridine and pyrimidine; C₂~C₆ heterocyclic ring comprising one or more N, O or S such as tetrahydrofuran, tetrahydropyran, piperidine, morpholine, thiomorpholine and so on; and R³ is aryl; heteroaryl such as furan, thiophene, imidazole, pyrrole, pyridine, pyrimidine and so on; aryl or heteroaryl substituted by one or more halogen, nitro, amino, C₁~C₆ alkyl, and C₁~C₆ alkyl substituted by one or more halogen; C₂~C₆ heterocyclic ring comprising one or more N, O or S such as tetrahydrofuran, tetrahydropyran, piperidine, morpholine, thiomorpholine and so on; C₁~C₁₈ alkyl; C₁~C₁₈ alkenyl; C₃~C₁₀ cycloalkyl; mono- or di- C₁~C₆ alkylamino; C₁~C₆ alkylcarbonylamino; di(C₁~C₆ alkylcarbonyl)amino; arylcarbonylamino; di(arylcarbonyl)amino.

Preferably,

R¹ is phenyl; heteroaryl such as furan, thiophene, pyrrole; phenyl substituted by one or more group selected from halogen, C₁~C₆ alkyl, C₁~C₆ alkoxy; styrene;

R² is hydrogen; halogen; C₁~C₆ alkyl; amino; cyano; di(C₁~C₃ alkylcarbonyl)amino; benzyloxy; and R³ is phenyl; heteroaryl such as furan and thiophene; phenyl substituted by one or more halogen, nitro; morpholine; C₁~C₁₈ alkyl; C₁~C₁₈ alkenyl; cyclohexane; benzoylamino.

Further preferred compounds among the O-acyloxime derivatives according to the present invention are listed as follows, and their structures are shown in Table 1.

1) (E)-benzaldehyde-O-benzoyloxime,
2) (E)-benzaldehyde-O-morpholine-4-carbonyloxime,
3) (E)-benzaldehyde-O-cyclohexanecarbonyloxime,
4) (E)-benzaldehyde-O-benzoylthiocarbamic acid oxime
5) (E)-benzaldehyde-O-thiophene-2-carbonyloxime,
6) (E)-benzaldehyde-O-furan-2-carbonyloxime,
7) (E)-4-fluorobenzaldehyde O-benzoyloxime,
8) (E)-4-fluorobenzaldehyde O-4-fluorobenzoyloxime,
9) (E)-4-fluorobenzaldehyde O-morpholine-4-carbonyloxime,
10) (E)-(3,5-di-t-butyl)-4-methoxybenzaldehyde O-benzoyloxime,
11) (E)-3-phenylpropenaldehyde O-benzoyloxime,
12) (E)-1-amino-benzaldehyde O-benzoyloxime,
13) (E)-1-N,N-diacetylamino-benzaldehyde O-benzoyloxime,
14) (E)-1-cyano-benzaldehyde O-benzoyloxime,
15) (E)-1-chloro-benzaldehyde O-benzoyloxime,
16) (E)-1-benzoic acid-benzaldehyde O-benzoyloxime,
17) (L)-2-furan-2-carboaldehyde O-benzoyloxime,
18) (E)-2-thiophene-2-carboaldehyde O-benzoyloxime,
19) (E)-1-phenylethanonaldehyde O-benzoyloxime,
20) (E)-N-4-fluorobenzylpyrrole-2-carboaldehyde O-benzoyloxime,
21) (E)-3,4-di-fluorobenzaldehyde O-benzoyloxime,
22) (E)-3,4-di-fluorobenzaldehyde O-morpholine-4-carbonyloxime,
23) (E)-3,4-di-fluorobenzaldehyde O-4-fluorobenzoyloxime,
24) (E)-3,4-di-fluorobenzaldehyde O-oleyloxime,
(E)-3,4-di-fluorobenzaldehyde O-linoleyloxime,
(E)-3,4-di-fluorobenzaldehyde O-decanoyloxime,
(E)-3,4-di-fluorobenzaldehyde O-4-nitro)benzoyloxime,
(E)-3,4-di-fluorobenzaldehyde O-3,4-difluorobenzoyloxime,
(E)-2,3-di-fluorobenzaldehyde O-benzoyloxime,
(E)-2,3-di-fluorobenzaldehyde O-morpholine-4-carbonyloxime,
31) (E)-2,4-di-fluorobenzaldehyde O-benzoyloxime,
32) (E)-2,4-di-fluorobenzaldehyde O-morpholine-4-carbonyloxime,
33) (E)-2,4-di-fluorobenzaldehyde O-4-fluorobenzoyloxime,
34) (E)-2,6-di-fluorobenzaldehyde O-benzoyloxime,
35) (E)-2,6-di-fluorobenzaldehyde O-morpholine-4-carbonyloxime,
36) (E)-3,5-di-fluorobenzaldehyde O-benzoyloxime,
37) (E)-3,5-di-fluorobenzaldehyde O-morpholine-4-carbonyloxime, and
38) (E)-2,5-di-fluorobenzaldehyde O-morpholine-4-carbonyloxime.

TABLE 1

| Compound | Structure |
|---|---|
| 1 | 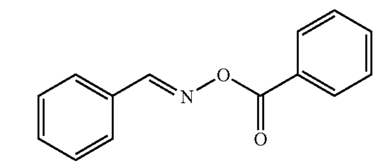 |
| 2 | 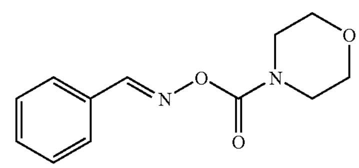 |
| 3 | 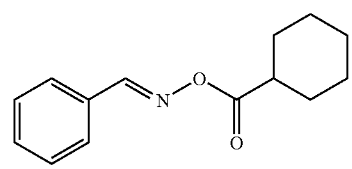 |
| 4 | 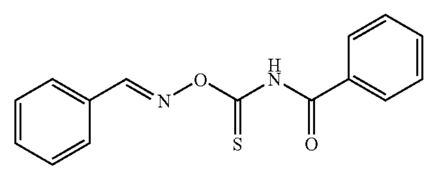 |
| 5 | 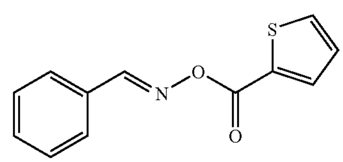 |
| 6 | 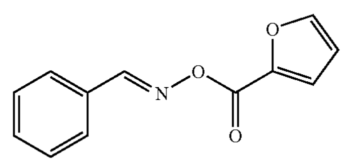 |
| 7 | 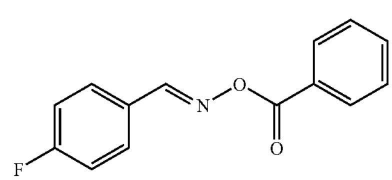 |

TABLE 1-continued
| Compound | Structure |
|---|---|
| 8 | 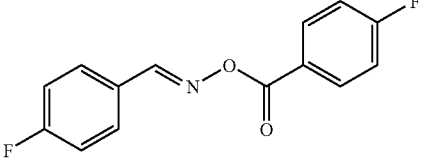 |
| 9 | 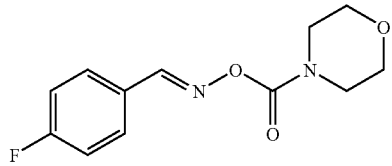 |
| 10 | 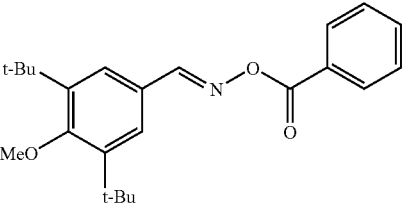 |
| 11 | 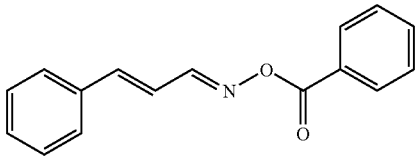 |
| 12 | 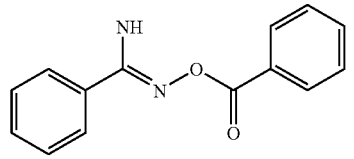 |
| 13 | 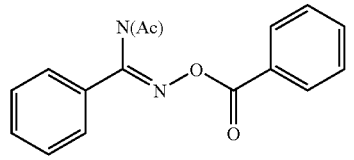 |
| 14 | 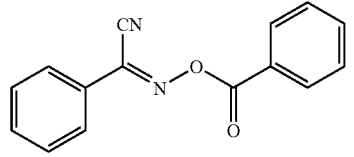 |
| 15 | 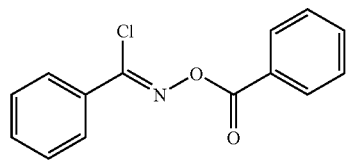 |
| 16 | 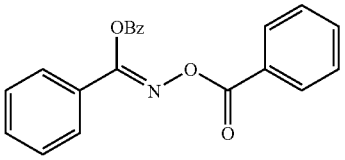 |
| 17 | 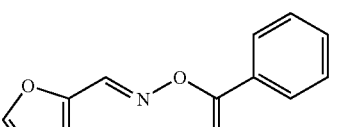 |
| 18 | 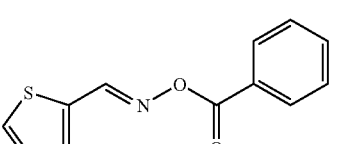 |
| 19 | 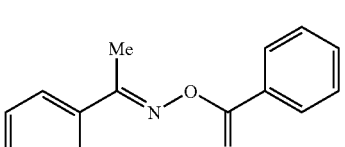 |
| 20 | 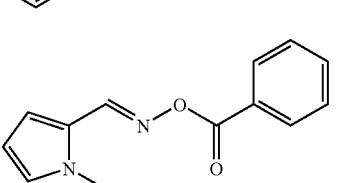 |
| 21 | 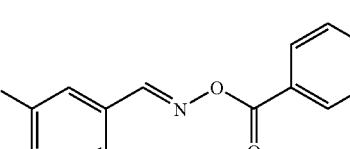 |
| 22 | 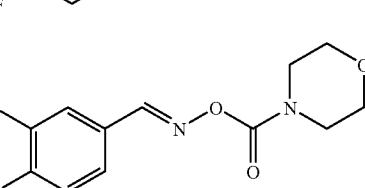 |
| 23 | 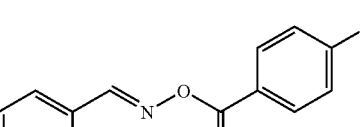 |
| 24 | 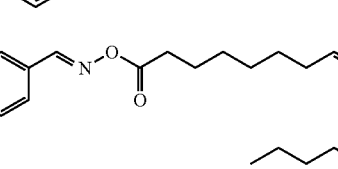 |

TABLE 1-continued

| Compound | Structure |
|---|---|
| 25 | 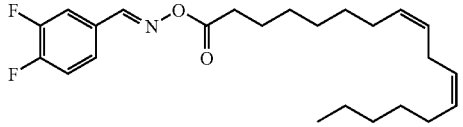 |
| 26 | 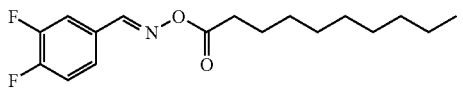 |
| 27 | 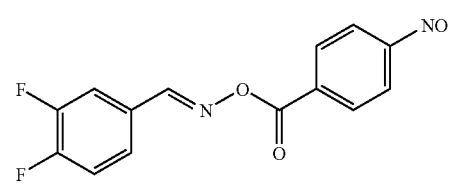 |
| 28 | 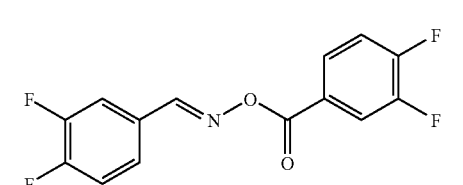 |
| 29 | 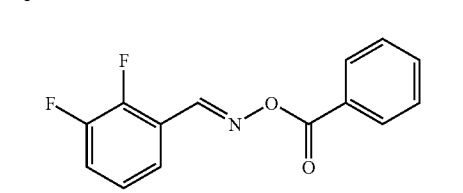 |
| 30 | 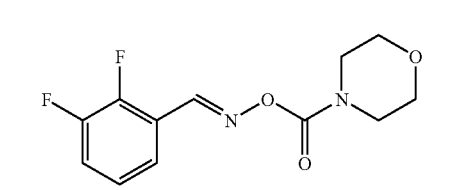 |
| 31 | 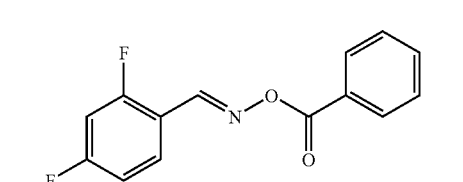 |
| 32 | 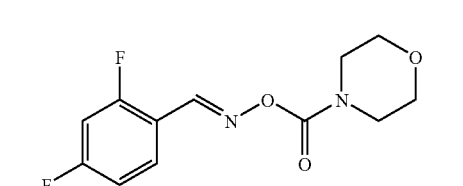 |
| 33 | 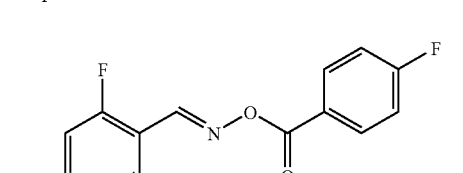 |
| 34 | 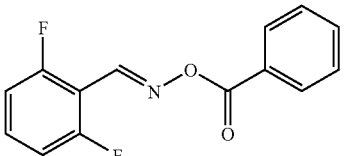 |
| 35 | 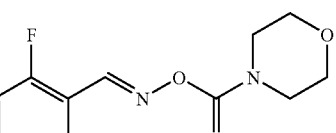 |
| 36 | 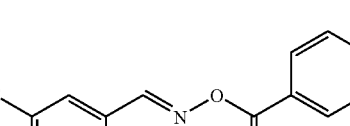 |
| 37 |  |
| 38 | 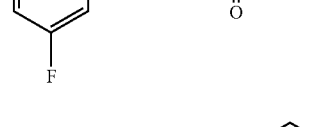 |

The O-acyloxime derivatives represented by Formula 1 may be used as forms of pharmaceutically acceptable salts thereof, and pharmaceutically acceptable free acids salts thereof are preparable. Both organic and inorganic acids may be used as the free acids. For example, the inorganic acids include hydrochloric acid, hydrobromic acid, sulfuric acid, and phosphoric acid, and the organic acids include citric acid, acetic acid, lactic acid, maleic acid, umaric acid, gluconic acid, methanesulfonic acid, glyconic acid, succinic acid, 4-toluenesulfonic acid, trifluoroacetic acid, galutronic acid, embonic acid, glutamic acid, and aspartic acid.

Additionally, the present invention provides a preparation method of O-acyloxime derivatives represented by the following Chemical Reaction scheme 1.

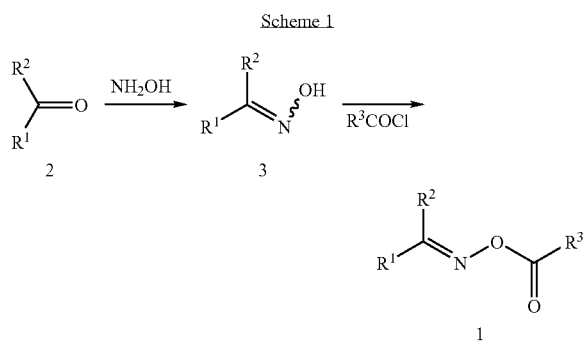

Scheme 1 wherein, $R^1$, $R^2$, and $R^3$ are same as defined in Formula 1.

A preparation method for O-acyloxime derivatives according to the present invention contains the steps of:

1) obtaining a compound 3 by reacting a compound 2 with hydroxyamine under the presence of base, and 2) obtaining a compound 1 by reacting the compound 3 prepared in the step 1) with acylchloride.

The preparation method of O-acyloxime derivatives according to the present invention will be described in more detail as follows.

In the step 1, the base includes metal hydroxides such as sodium hydroxide, potassium hydroxide, and lithium hydroxide; basic salts such as sodium carbonate, potassium carbonate, cesium carbonate, sodium bicarbonate, and sodium acetate; aromatic amines such as pyridine and lutidine; and tertiary amines such as triethylamine, tripropylamine, tributylamine, cyclohexyldimethylamine, 4-dimethylaminopyridine, N,N-dimethylaniline, N-methylpiperidine, N-methylpyrrolidine, and N-methylmorpholine. Triethylamine is preferable.

Water, $C_1$~$C_3$ low alcohol, or a mixture thereof is preferably used as a reaction solvent, and ethanol is most preferably used.

Reaction temperature is preferably room temperature. Reaction time is preferably 30 min 24 hrs, and is most preferably 1~20 hrs.

Additionally, the compound 3 may be formed as a mixture of isomers, and the isomers may be separated by conventional methods such as column chromatography.

In the step 2, the reaction may be performed either under the presence or absence of a base. The base includes metal hydroxides such as sodium hydroxide, potassium hydroxide, lithium hydroxide; basic salts such as sodium carbonate, potassium carbonate, cesium carbonate, sodium bicarbonate, and sodium acetate; aromatic amines such as pyridine and lutidine; and tertiary amines such as triethylamine, tripropylamine, tributylamine, cyclohexyldimethylamine, 4-dimethylaminopyridine, N,N-dimethylaniline, N-methylpiperidine, N-methylpyrrolidine, and N-methylmorpholine. Triethylamine or sodium hydride is preferable.

Additionally, sulfuric acid ($H_2SO_4$) may be used as a catalyst in the reaction, and dichloromethane, THF, or acetyl anhydride is preferably used as a reaction solvent.

The reaction temperature is preferably about $-5°$ C.~$+5°$ C., and is most preferably $0°$ C. The compound 3 may be prepared by a method disclosed in the prior art or a similar method thereto, or is a commercially available compound may also be used.

Additionally, the O-acyloxime derivative of the compound 1 prepared in the above may be formed as a mixture of isomers, and the isomers may be separated by conventional methods such as column chromatography.

Additionally, the O-acyloxime derivative of the compound 1 may be prepared by reaction of the compound 2 of more than 2 equivalents with $NH_2OH$ under the presence of a base, without passing through the step 2.

Additionally, the present invention provides a pharmaceutical composition for prevention and treatment of cardiovascular disease, containing O-acyloxime derivatives of Formula 1 as active ingredients.

O-acyloxime derivatives according to the present invention have excellent inhibitory effect on $Lp$-$PLA_2$, and thereby may effectively be used for prevention and treatment of cardiovascular disease caused by $Lp$-$PLA_2$ such as hyperlipidemia, coronary arterial heart disease, atherosclerosis, and myocardial infarction.

The composition according to the present invention may further include one or more active ingredients having the same or similar function in addition to the O-acyloxime derivatives.

For the prevention and treatment of cardiovascular disease, the composition according to the present invention may be used independently or together with an operation, hormone treatment, pharmaceutical treatment and biological reaction controller.

The composition according to the present invention may be prepared by adding one or more pharmaceutically acceptable carriers in addition to the above active ingredients. The pharmaceutically acceptable carriers include saline solution, sterile water, Ringer's solution, buffered saline solution, dextrose solution, maltodextrin solution, glycerol, ethanol, and a mixture thereof, and may further include other conventional additives such as antioxidant, buffer solution, and bacteriostat, if necessary. Additionally, the composition may be formulated in various forms of injection such as solution, suspension, and emulsion; pill, capsule, granule, or tablet by further adding diluent, dispersant, surfactant, bonding agent, and lubricant. Furthermore, the composition may be formulated with a proper method known in the art or a method disclosed by Remington's Pharmaceutical Science (the latest edition, Mack Publishing Company, Easton Pa.), according to the component or kinds of disease.

The composition according to the present invention may be prepared for oral administration, parenteral administration such as intravenous, subcutaneous, intraperitoneal administration, or local application. The dosage varies according to the weight, age, sex, and health condition of patients, diet pattern, dosing intervals, dosing method, excretion rate, and state of disease. Daily dosage of O-acyloxime derivatives of Formula 1 is about 0.1~100 mg/kg, preferably 0.5~10 mg/kg, and it is more preferable to dose one to several times a day.

According to the result of toxicity test carried out by oral administration of the O-acyloxime derivative according to the present invention, lethal dose $50(LD_{50})$ of the O-acyloxime derivative is more than 1,000 mg/kg.

DETAILED DESCRIPTION OF EXEMPLARY EMBODIMENTS OF THE INVENTION

Hereinafter, preferred example embodiments of the present invention will be described more fully for easier understanding. This invention may, however, be embodied in many different forms and should not be construed as limited to the example embodiments set forth herein.

EXAMPLE 1

Preparation of (E)-benzaldehyde O-benzoyloxime

After dissolving benzaldehyde (5 ml, 49 mmol) in ethanol (100 ml), hydroxyamine ($NH_2OH$) (4.4 g, 64.0 mmol) and triethylamine (9 ml, 64.0 mmol) were added. After stirring reaction solution for 1 hour at room temperature, the solvent was removed. After adding water (50 ml), the solution was extracted with ethylacetate. The obtained residue was then separated into (E)-oxime compound (3 g, 50%) and (2)-oxime compound (0.32 g, 5.4%) by column chromatography.

After dissolving the obtained (E)-oxime compound (0.22 g, 1.8 mmol) in dichloromethane, benzoylchloride (0.3 ml, 2.3 mmol) was slowly added at 0° C. under the presence of triethylamine. After stirring the reaction solution for 1 hour, the reaction was quenched by 1N hydrochloric acid, and the reaction solution was extracted with dichloromethane. A pure compound of (E)-benzaldehyde O-benzoyloxime 1 (0.26 g, 65%) was obtained by separating residue with silica gel column chromatography.

Additionally, after dissolving the obtained (Z)-oxime compound (0.1 g, 0.83 mmol) in dichloromethane, reaction solution was cooled to −40° C., and benzoylchloride (0.12 ml, 1.07 mmol) was added. After stirring for 20 minutes, a compound of (E)-benzaldehyde O-benzoyloxime (1) (0.11 g, 61%) was obtained by the same method as that of the (E)-oxime compound preparation.

$^1$H NMR (300 $^{MHz}$, $CDCl_3$) 7.48 (m, 5H), 7.62 (m, 1H), 7.82 (dd, J=1.8, 7.8 Hz, 2H), 8.14 (dd, J=2.1, 8.4 Hz, 2H), 8.57 (s, 1H).

EXAMPLE 2

Preparation of (E)-benzaldehyde O-morpholine-4-carbonyloxime

After dissolving benzaldehyde (1.0 ml, 9.8 mmol) in ethanol (20 ml), hydroxyamine (0.88 g, 12.8 mmol) and triethylamine (1.77 ml, 12.8 mmol) were added. After stirring reaction solution for 1 hour at room temperature, the solvent was removed. After adding water (50 ml), the solution was extracted with ethylacetate. (L)- and (2)-oxime mixtures (1.00 g, 85%) were obtained by separating the residue with column chromatography.

After dissolving the (E)- and (Z)-oxime mixtures (1.0 g, 8.26 mmol) in THF (30 ml), morpholinecarbonylchloride (1.23 ml, 10.7 mmol) was slowly added at 0° C. under the presence of NaH (0.26 g, 10.7 mmol). After stirring the reaction solution for 1 hour, the reaction was quenched by 1 N hydrochloric acid, and the reaction solution was extracted with dichloromethane. A pure compound of (E)-benzaldehyde O-morpholine-4-carbonyloxime (2) (1.8 g, 93%) was obtained by separating the residue with silica gel column chromatography.

$^1$H NMR (300 $^{MHz}$, $CDCl_3$) 3.57 (t, J=4.9 Hz, 4H), 3.71 (t, J=4.6 Hz, 4H), 7.45 (m, 3H), 7.73 (d, J=7.8 Hz, 2H), 8.31 (s, 1H)

EXAMPLE 3

Preparation of (E)-benzaldehyde-O-cyclohexanecarbonyloxime

The title compound was prepared in the same method as Example 1 except that cyclohexanecarbonylchloride was used instead of benzoylchloride.

$^1$H NMR (300 $^{MHz}$, $CDCl_3$) 2.0~1.21 (m, 9H), 2.45 (m, 1H), 7.41 (m, 3H), 7.72 (dd, J=1,8, 7.8 Hz, 2H), 8.34 (s, 1H).

EXAMPLE 4

Preparation of (E)-benzaldehyde-O-benzoylthiocarbamic acid oxime

The title compound was prepared in the same method as Example 1 except that benzoylisocyanate was used instead of benzoylchloride.

$^1$H NMR (300 $^{MHz}$, $CDCl_3$) 7.46 (m, 6H), 7.60 (m, 1H), 7.80 (m, 2H), 8.12 (m, 2H), 8.55 (s, 1H).

EXAMPLE 5

Preparation of (E)-benzaldehyde-O-thiophene-2-carbonyloxime

The title compound was prepared in the same method as Example 1 except that thiophene-2-carbonylchloride was used instead of benzoylchloride.

$^1$H NMR (300 $^{MHz}$, $CDCl_3$) 7.16 (dd, J=3.6, 4.8 Hz, 1H), 7.48 (m, 3H), 7.63 (dd, J =1.2, 5.1 Hz, 1H), 7.81 (dd, J=1.8, 7.8 Hz, 2H), 7.94 (dd, J=1.2, 4.2 Hz, 1H), 8.51 (s, 1H).

EXAMPLE 6

Preparation of (E)-benzaldehyde-O-furan-2-carbonyloxime

The title compound was prepared in the same method as Example 1 except that furan-2-carbonylchloride was used instead of benzoylchloride.

$^1$H NMR (300 $^{MHz}$, $CDCl_3$) 6.54 (q, J=1.8 Hz, 1H), 7.30 (d, J=3.6 Hz, 1H), 7.45 (m, 3H), 7.63 (s, 1H), 7.76 (t, J=4.1 Hz), 8.50 (s, 1H).

EXAMPLE 7

Preparation of (E)-4-fluorobenzaldehyde O-benzoyloxime

The title compound was prepared in the same method as Example 1 except that 4-fluorobenzaldehyde was used instead of benzaldehyde.

$^1$H NMR (300 $^{MHz}$, $CDCl_3$) 7.1 4 (t like, J=8.7 Hz, 2H), 7.49 (t like, J=7.2 Hz, 2H), 7.61 (t like, J=7.7 Hz, 1H), 7.82 (dd, J=5.4, 8.4 Hz, 2H), 8.12 (d, J=7.2 Hz, 2H), 8.53 (s, 1H).

EXAMPLE 8

Preparation of (E)-4-fluorobenzaldehyde O-4-fluorobenzoyloxime

The title compound was prepared in the same method as Example 1 except that 4-fluorobenzaldehyde and 4-fluorobenzoylchloride were used instead of benzaldehyde and benzoylchloride.

$^1$H NMR (300 $^{MHz}$, CDCl$_3$) 7.1 5 (m, 4H), 7.80 (dd, J=5.3, 8.9 Hz, 2H), 8.12 (dd, J =5.4, 8.4 Hz, 2H), 8.50 (s, 1H)

EXAMPLE 9

Preparation of (E)-4-fluorobenzaldehyde O-morpholine-4-carbonyloxime

The title compound was prepared in the same method as Example 2 except that 4-fluorobenzaldehyde was used instead of benzaldehyde.

$^1$H NMR (300 $^{MHz}$, CDCl$_3$) 3.55 (t, J=4.9 Hz, 4H), 3.69 (t, J=4.6 Hz, 4H), 7.08 (t, J=8.6 Hz, 2H), 7.71 (dd, J=5.5, 9.1 Hz, 2H), 8.27 (s, 1H).

EXAMPLE 10

Preparation of (E)-(3,5-di-t-butyl)-4-methoxybenzaldehyde O-benzoyloxime

The title compound was prepared in the same method as Example 1 except that 3,5-di-t-butylbenzoylaldehyde was used instead of benzoylchloride.

$^1$H NMR (300 $^{MHz}$, CDCl$_3$) 1.44 (s, 1 8H), 3.72 (s, 3H), 7.44 (m, 5H, 7.66 (s, 2H), 8.51 (s, 1H).

EXAMPLE 11

Preparation of (E)-3-phenylpropenaldehyde O-benzoyloxime

The title compound was prepared in the same method as Example 1 except that 3-phenylpropenaldehyde was used instead of benzaldehyde.

$^1$H NMR (300 $^{MHz}$, CDCl$_3$) 7.11 (m, 2H), 7.40 (m, 3H), 7.50 (m, 3H), 7.60 (m, 2H), 8.13 (m, 2H), 8.35 (dd, J=7.2, 7.8 Hz, 1H).

EXAMPLE 12

Preparation of (E)-1-amino-benzaldehyde O-benzoyloxime

After dissolving benzonitrile (10.3 ml, 100 mmol) in ethanol (50 ml), hydroxyamine (9.02 g, 130 mmol) and sodium carbonate (13.76 g, 130 mmol) were added. After refluxing reaction solution for 6 hours, hydroxyamine (9.02 g, 130 mmol) and sodium carbonate (13.76 g, 130 mmol) were added, and the reaction solution was further refluxed for 14 hours. After removing the solvent, water (50 ml) was added and the solution was extracted with ethylacetate. (E)- and (Z)-oxime mixtures (1 2.6 g, 92.5%) were obtained by separating the residue with column chromatography.

After dissolving the (E)- and (Z)-oxime mixtures (0.73 g, 5.36 mmol) in CH$_2$Cl$_2$ (30 ml), benzoylchloride (0.81 ml, 6.79 mmol) was slowly added at 0° C. under the presence of triethylamine(0.97 ml, 6.79 mmol). After stirring the reaction solution for 1 hour, the reaction was quenched by 1 N hydrochloric acid, and the reaction solution was extracted with dichloromethane. A pure compound of E()-1-amino-benzaldehyde O-benzoyloxime (12) (0.98 g, 75.9%) was obtained by separating the residue with silica gel column chromatography.

$^1$H NMR (300 $^{MHz}$, CDCl$_3$) 5.35 (s, 2H, —NH2), 7.47~7.34 (m, 5H), 7.58 (m, 1H), 7.72 (m, 2H), 8.05 (s, 2H).

EXAMPLE 13

Preparation of (E)-1-N,N-diacetylamino-benzaldehyde O-benzoyloxime

After dissolving the (E)-1-amino-benzaldehyde O-benzoyloxime (0.2 g, 0.83 mmol) obtained from Example 12 in acetic anhydride (10 ml), H$_2$SO$_4$ (0.1 ml, catalystic amount) was added. After stirring reaction solution for 6 hours, water was added and the reaction solution was extracted with dichloromethane. A pure compound of (E)-1-N,N-diacetylamino-benzaldehyde O-benzoyloxime (13) (0.23 g, 85%) was obtained by separating the residue with silica gel column chromatography.

$^1$H NMR (300 $^{MHz}$, CDCl$_3$) 2.44 (s, 6H), 7.50 (m, 5H), 7.63 (m, 1H), 7.88 (m, 2H), 7.99 (m, 2H).

EXAMPLE 14

Preparation of (E)-1-cyano-benzaldehyde O-benzoyloxime

After dissolving 2-hydroxyimino-2-phenylacetonitrile (1.0 g, 6.84 mmol) in CH$_2$Cl$_2$ (30 ml), benzoylchloride(1.02 ml, 8.89 mmol) was slowly added at 0° C. under the presence of triethylamine (1.24 ml, 8.89 mmol). After stirring reaction solution for 1 hour, the reaction was quenched by 1 N hydrochloric acid and the reaction solution was extracted with dichloromethane. A pure compound of (E)-1-cyano-benzaldehyde O-benzoyloxime (14) (1.30 g, 81%) was obtained by separating the residue with silica gel column chromatography.

$^1$H NMR (300 $^{MHz}$, CDCl$_3$) 7.71 7.50 (m, 6H), 8.04 (m, 2H), 8.25 (m, 2H).

EXAMPLE 15

Preparation of (E)-1-chloro-benzaldehyde O-benzoyloxime

After dissolving (E)-benzaldehyde oxime (3.0 g, 25 mmol) in CH$_2$Cl$_2$ (30 ml), N-chlorosuccinimide (3.4 g, 25 mmol) was slowly added at 0° C. After stirring reaction solution for 2 hours, the reaction was completed by adding water (20 ml), and the reaction solution was extracted with dichloromethane. A pure compound of (E)-1-chloro-benzaldehyde oxime (3.30 g, 85%) was obtained by separating the residue with silica gel column chromatography. After dissolving the (E)- and (Z)-oxime mixtures (1.5 g, 9.64 mmol) in CH$_2$Cl$_2$ (30 ml), benzoylchloride (1.45 ml, 12.53 mmol) was slowly added at 0° C. under the presence of triethylamine (1.75 ml, 12.53 mmol). After stirring reaction solution for 1 hour, the reaction was quenched by 1 N hydrochloric acid, and the reaction solution was extracted with dichloromethane. A pure compound of (E)-1-chloro-benzaldehyde O-benzoyloxime (15) (1.9 g, 76%) was obtained by separating the residue with silica gel column chromatography.

$^1$H NMR (300 $^{MHz}$, CDCl$_3$) 7.52 (m, 5H), 7.67 (m, 1H), 8.05 (m, 2H), 8.20 (m, 2H).

EXAMPLE 16

Preparation of (E)-1-benzoic acid-benzaldehyde O-benzoyloxime

After dissolving benzoylchloride(1.0 g, 7.11 mmol) in ethanol (20 ml), hydroxyamine (0.59 g, 8.53 mmol) and tri-ethylamine (1.18 ml, 8.53 mmol) were added. After stirring reaction solution for 30 minutes at room temperature, the solvent was removed. After adding water (50 ml), the solution was extracted with ethylacetate. (E)-1-benzoicacid-benzaldehyde O-benzoyloxime (16) (1.5 g, 61 %) was obtained by separating the residue with column chromatography.

$^1$H NMR (300 $^{MHz}$, CDCl$_3$) 7.29 (m, 2H), 7.43 7.61 (m, 6H), 7.74 (m, 1H), 7.86 (m, 2H), 7.99 (m, 2H), 8.26 (m, 2H).

EXAMPLE 17

Preparation of (E)-2-furan-2-carboaldehyde O-benzoyloxime

The title compound was prepared in the same method as Example 1 except that 2-furan-2-carbonylaldehyde was used instead of benzaldehyde.

$^1$H NMR (300 $^{MHz}$, CDCl$_3$) 6.55 (dd, J=3.6, 3.6 Hz, 1H), 7.00 (d, J=3.9 Hz, 1H), 7.48-7.61 (m, 4H), 8.11 (d, J=2.1, 6.6 Hz, 2H).

EXAMPLE 18

Preparation of (E)-2-thiophene-2-carboaldehyde O-benzoyloxime

The title compound was prepared in the same method as Example 1 except that 2-thiophene-2-carbonylaldehyde was used instead of benzaldehyde.

$^1$H NMR (300 $^{MHz}$, CDCl$_3$) 7.13 (dd, J=4.8, 4.8 Hz, 1H), 7.46-7.64 (m, 5H), 8.10 (dd, J=1.8, 6.6 Hz, 2H), 8.71 (s, 1H).

EXAMPLE 19

Preparation of (E)-1-phenylethanonaldehyde O-benzoyloxime

The title compound was prepared in the same method as example 1 except that acetophenone was used instead of benzaldehyde.

$^1$H NMR(300 $^{MHz}$, CDCl$_3$) 2.53 (s, 3H), 7.42~7.53 (m, 5H), 7.62 (m, 1H), 7.83 (m, 2H), 8.14 (dd, J=1.2, 7.2 Hz, 2H).

EXAMPLE 20

Preparation of (E)-N-4-fluorobenzylpyrrole-2-carboaldehyde O-benzoyloxime

The title compound was prepared in the same method as example 1 except that N-fluorobenzylpyrrole-2-carbonylaldehyde was used instead of benzaldehyde.

$^1$H NMR (300$^{MHz}$, CDCl$_3$) 5.57 (s, 2H), 6.27 (t, J=3.3 Hz, 1H), 6.63 (dd, J=1.5, 3.9 Hz, 1H), 6.99 (m, 4H), 7.28 (m, 1H), 7.47 (m, 2H), 7.59 (m, 1H), 8.07 (m, 2H), 8.37 (s, 1H).

EXAMPLE 21

Preparation of (E)-3,4-di-fluorobenzaldehyde O-benzoyloxime

The title compound was prepared in the same method as Example 1 except that 3,4-di-fluorobenzaldehyde was used instead of benzaldehyde.

$^1$H NMR (300 $^{MHz}$, CDCl$_3$) 7.25 (m, 1H), 7.50 (m, 3H), 7.63 (m, 1H), 7.73 (m, 1H), 8.12 (dd, J=1.8, 9.9 Hz, 2H), 8.50 (s, 1H).

EXAMPLE 22

Preparation of (E)-3,4-di-fluorobenzaldehyde O-morpholine-4-carbonyloxime

The title compound was prepared in the same method as example 2 except that 3,4-di-fluoroaldehyde was used instead of benzaldehyde.

$^1$H NMR (300 $^{MHz}$, CDCl$_3$) 3.56 (t, J=5.0 Hz, 4H), 3.71 (t, J=4.7 Hz, 4H), 7.22 (m, 1H), 7.42 (m, 1H), 7.64 (m, 1H), 8.45 (s, 1H).

EXAMPLE 23

Preparation of (E)-3,4-di-fluorobenzaldehyde O-4-fluorobenzoyloxime

The title compound was prepared in the same method as Example 1 except that 3,4-di-fluorobenzaldehyde and 4-fluorobenzoylchloride were used instead of benzaldehyde and benzoylchloride.

$^1$H NMR (300 $^{MHz}$, CDCl$_3$) 7.17 (m, 2H), 7.26 (m, 1H), 7.52 (m, 1H), 7.72 (m, 1H), 8.14 (m, 2H), 8.48 (s, 1H).

EXAMPLE 24

Preparation of (E)-3,4-di-fluorobenzaldehyde O-oleyloxime

The title compound was prepared in the same method as Example 1 except that 3,4-di-fluorobenzaldehyde and oleoylchloride were used instead of benzaldehyde and benzoylchloride.

$^1$H NMR (300$^{MHz}$, CDCl$_3$) 0.85 (t, J=6.3 Hz, 3H), 1.25 (m, 20H), 1.70 (m, 2H), 1.99 (m, 4H), 2.44 (t, J=7.2 Hz, 2H), 5.34 (m, 2H), 7.20 (m, 1H), 7.42 (m, 1H), 7.64 (m, 1H), 8.28 (s, 1H).

EXAMPLE 25

Preparation of (E)-3,4-di-fluorobenzaldehyde O-linoleyloxime

The title compound was prepared in the same method as Example 1 except that 3,4-di-fluorobenzaldehyde and linoleylchloride were used instead of benzaldehyde and benzoylchloride.

$^1$H NMR (300 $^{MHz}$, CDCl$_3$) 0.89 (t, J=6.6 Hz, 3H), 1.23-1.41 (m, 14H), 1.73 (m, 2H), 2.05 (m, 4H), 2.46 (t, J=7.2 Hz,

2H), 2.77 (t, J=6.3 Hz, 2H), 5.35 (m, 4H), 7.22 (m, 1H), 7.44 (m, 1H), 7.65 (m, 1H), 8.29 (s, 1H).

EXAMPLE 26

Preparation of (E)-3,4-di-fluorobenzaldehyde O-decanoyloxime

The title compound was prepared in the same method as Example 1 except that 3,4-di-fluorobenzaldehyde and decanoylchloride were used instead of benzaldehyde and benzoylchloride.

$^1$H NMR (300 $^{MHz}$, CDCl$_3$) 0.88 (t, J=6.6 Hz, 3H), 1.34 (m, 12H), 1.73 (m, 2H), 2.47 (t, J=7.2 Hz, 2H), 7.23 (m, 1H), 7.44 (m, 1H), 7.65 (m, 1H), 8.29 (s, 1H).

EXAMPLE 27

Preparation of (E)-3,4-di-fluorobenzaldehyde O-(4-nitro)benzoyloxime

The title compound was prepared in the same method as Example 1 except that 3,4-di-fluorobenzaldehyde and 4-nitrobenzoylchloride were used instead of benzaldehyde and benzoylchloride.

$^1$H NMR (300 $^{MHz}$, CDCl$_3$) 7.28 (m, 1H), 7.52 (m, 1H), 7.74 (m, 1H), 8.33 (dd, J=9.0, 9.0 Hz, 4H), 8.53 (s, 1H).

EXAMPLE 28

Preparation of (E)-3,4-di-fluorobenzaldehyde O-3,4-difluorobenzoyloxime

The title compound was prepared in the same method as Example 1 except that 3,4-di-fluorobenzaldehyde and 3,4-difluorobenzoylchloride was used instead of benzaldehyde and benzoylchloride.

$^1$H NMR (300 $^{MHz}$, CDCl$_3$) 7.28 (m, 3H), 7.51 (m, 1H), 7.73 (m, 1H), 7.94 (m, 2H), 8.49 (s, 1H).

EXAMPLE 29

Preparation of (E)-2,3-di-fluorobenzaldehyde O-benzoyloxime

The title compound was prepared in the same method as Example 1 except that 2,3-di-fluorobenzaldehyde was used instead of benzaldehyde.

$^1$H NMR (300 $^{MHz}$, CDCl$_3$) 7.16 (m, 1H), 7.29 (m, 1H), 7.50 (t, J=7.7 Hz, 2H), 7.63 (m, 1H), 7.88 (m, 1H), 8.13 (m, 2H), 8.82 (s, 1H).

EXAMPLE 30

Preparation of (E)-2,3-di-fluorobenzaldehyde O-morpholine-4-carbonyloxime

The title compound was prepared in the same method as Example 2 except that 2,3-di-fluorobenzaldehyde was used instead of benzaldehyde.

$^1$H NMR (300 $^{MHz}$, CDCl$_3$) 3.57 (t, J=4.9 Hz, 4H), 3.71 (t, J=4.8 Hz, 4H), 7.10 (m, 1H), 7.25 (m, 1H), 7.79 (dd, J=6.2, 8.9 Hz, 1H), 8.57 (s, 1H).

EXAMPLE 31

Preparation of (E)-2,4-di-fluorobenzaldehyde O-benzoyloxime

The title compound was prepared in the same method as Example 1 except that 2,4-di-fluorobenzaldehyde was used instead of benzaldehyde.

$^1$H NMR (300 $^{MHz}$, CDCl$_3$) 6.88 (m, 1H), 6.97 (m, 1H), 7.50 (m, 2H), 7.61 (m, 1H), 8.12 (m, 3H), 8.75 (s, 1H).

EXAMPLE 32

Preparation of (E)-2,4-di-fluorobenzaldehyde O-morpholine-4-carbonyloxime

The title compound was prepared in the same method as Example 2 except that 2,4-di-fluorobenzaldehyde was used instead of benzoylchloride.

$^1$H NMR (300 $^{MHz}$, CDCl$_3$) 3.55 (t, J=4.8 Hz, 4H), 3.69 (t, J=4.6 Hz, 4H), 6.84 (m, 1H), 6.91 (m, 1H), 8.04 (m, 1H), 8.50 (s, 1H).

EXAMPLE 33

Preparation of (E)-2,4-di-fluorobenzaldehyde O-4-fluorobenzoyloxime

The title compound was prepared in the same method as Example 1 except that 2,4-di-fluorobenzaldehyde and 4-fluorobenzoylchloride were used instead of benzaldehyde and benzoylchloride.

$^1$H NMR (300 $^{MHz}$, CDCl$_3$) 6.93 (m, 2H), 7.16 (t, 2H, J=8.6 Hz), 8.15 (m, 3H), 8.75 (s, 1H).

EXAMPLE 34

Preparation of (E)-2,6-di-fluorobenzaldehyde O-benzoyloxime

The title compound was prepared in the same method as Example 1 except that 2,6-di-fluorobenzaldehyde was used instead of benzaldehyde.

$^1$H NMR (300 $^{MHz}$, CDCl$_3$) 7.02 (t, J=8.4 Hz, 2H), 7.47 (m, 3H), 7.62 (t, J=7.2 Hz), 8.12 (m, 1H), 8.76 (s, 1H).

EXAMPLE 35

Preparation of (E)-2,6-di-fluorobenzaldehyde O-morpholine-4-carbonyloxime

The title compound was prepared in the same method as Example 2 except that 2,6-di-fluorobenzaldehyde was used instead of benzaldehyde.

$^1$H NMR (300 $^{MHz}$, CDCl$_3$) 3.54 (t, J=4.8 Hz, 4H), 3.68 (t, J=4,7 Hz, 4H), 7.08 (m, 2H), 7.70 (m, 1H), 8.50 (s, 1H).

EXAMPLE 36

Preparation of (E)-3,5-di-fluorobenzaldehyde O-benzoyloxime

The title compound was prepared in the same method as example 1 except that 3,5-di-fluorobenzaldehyde was used instead of benzaldehyde.

¹H NMR (300 $^{MHz}$, CDCl₃) 6.95 (m, 1H), 7.36 (m, 2H), 7.53 (m, 2H), 7.63 (m, 1H), 8.12 (m, 2H), 8.50 (s, 1H).

EXAMPLE 37

Preparation of (E)-3,5-di-fluorobenzaldehyde O-morpholine-4-carbonyloxime

The title compound was prepared in the same method as Example 2 except that 3,5-di-fluorobenzaldehyde was used instead of benzaldehyde.

¹H NMR (300 $^{MHz}$, CDCl₃) 3.55 (t, J=4.8 Hz, 4H), 3.68 (t, J=4.8 Hz, 4H), 6.95 (t, J=8.6 Hz, 2H), 7.38 (m, 1H), 8.48 (s, 1H).

EXAMPLE 38

Preparation of (E)-2,5-di-fluorobenzaldehyde O-morpholine-4-carbonyloxime

The title compound was prepared in the same method as Example 2 except that 2,5-di-fluorobenzaldehyde was used instead of benzaldehyde.

¹H NMR (300 $^{MHz}$, CDCl₃) 3.56 (t, J=4.9 Hz, 4H), 3.71 (t, J=4.9 Hz, 4H), 6.90 (m, 1H), 7.28 (m, 2H), 8.24 (s, 1H).

EXPERIMENTAL EXAMPLE 1

The Eeffect of O-acyloxime Derivatives According to the Present Invention on Lp-PLA₂ Activity The following tests were carried out to analyze the effect of O-acyloxime derivatives according to the present invention on Lp-PLA₂ activity.

1. Preparation of Enzyme Sources

Blood was collected from normal lipidemic volunteers. EDTA was used as anticoagulant (1.5 mg/ml of blood). After low-speed centrifugation of the whole blood to obtain plasma and to prevent lipoprotein modification, EDTA (0.1%), NaN₃ (0.05 %), and PMSF (0.01 5%) were added. LDL was isolated from the plasma by discontinuous density gradient ultra centrifugation. Briefly, the plasma was centrifuged at 100,000×g at 4° C. for 20 hours. After the top layers containing chylomicron and very low-density lipoprotein (VLDL) were removed, the density of remaining plasma fractions was increased to 1.064 g/$^{ml}$ with NaBr solution, and then they were recentrifuged at 100,000×g for an additional 24 hours. The LDL fraction in the top of the tube was collected and dialyzed overnight against three changes of phosphate buffer (pH 7.4), containing NaCl (150 mM), in the dark at 4° C. to remove NaBr and EDTA. The LDL in PBS was stored at 4° C. and used within 4 weeks. The purity of the fraction was confirmed by agarose gel electrophoresis and SDS-PAGE. Concentration of LDL protein was determined using bovine serum albumin (BSA) as a standard.

2. Measurement of Lp-PLA₂ Activity

A method partially modified from the method of Boyd et al. (*Bioorg. Med. Chem. Lett.*, 2000, 10, 2557-2561) was used. Lp-PLA₂, the enzyme is also known as platelet-activating factor acetylhydrolase (PAF-AH), activity was measured using [³H]PAF as a substrate. Briefly, a micelle substrate was prepared with unlabelled PAF and [³H]PAF (100 μCi/mL, 21.5 Ci/mmole, NET 910) in 10 mM phosphate-buffered saline (PBS), pH 7.4, containing 2.7 mM EDTA (PBS-EDTA). The reaction mixture, containing 20 μL of diluted human LDL (Lp-PLA₂ source, 4-5 pg protein), 120 μL of PBS-EDTA, and 20 μL of test sample, was preincubated at 37° C. for 15 min. The reaction was initiated by the addition of 40 μL micelle substrate (0.1 μCi, final conc. 80 μM PAF) to measure initial rates of PAF-AH activity. The reaction was stopped by vortexing with 600 μL of CHCl₃/MeOH (2: 1) and the CHCl₃ and aqueous layers were separated by centrifugation. The aqueous layer was removed (250 μL) and vortexed with 250 μL of CHCl₃. The aqueous layer was again removed and the [³H]acetate determined by scintillation counting (1450 Microbeta Trilux, Qallac Oy, Turku, Finland). The raw counts were corrected for background using a nonenzyme-containing blank and were expressed as nanomoles of PAF degraded per hour per milligram of protein.

A portion of the test results is shown in table 2, and figures show average values of two test results.

TABLE 2

| Sample | | IC₅₀ (μM)$^a$ |
|---|---|---|
| Example 1 | [structure] | 3.8 |
| Example 7 | [structure] | 4.4 |

TABLE 2-continued

| Sample | | IC$_{50}$ (μM)$^a$ |
|---|---|---|
| Example 10 | [structure: 3,5-di-t-Bu-4-MeO-C6H2-CH=N-O-C(=O)-Ph] | 11%$^b$ |
| Example 11 | [structure: Ph-CH=CH-CH=N-O-C(=O)-Ph] | 25.0 |
| Example 16 | [structure: Ph-C(OBz)=N-O-C(=O)-Ph] | 29%$^b$ |
| Example 18 | [structure: 2-thienyl-CH=N-O-C(=O)-Ph] | 26.0 |
| Example 19 | [structure: Ph-C(Me)=N-O-C(=O)-Ph] | 11.2 |
| Example 21 | [structure: 3,4-F2-C6H3-CH=N-O-C(=O)-Ph] | 2.0 |
| Example 24 | [structure: 3,4-F2-C6H3-CH=N-O-C(=O)-(CH2)7-CH=CH-(CH2)7-CH3] | 16%$^b$ |
| Example 25 | [structure: 3,4-F2-C6H3-CH=N-O-C(=O)-(CH2)7-CH=CH-CH2-CH=CH-(CH2)4-CH3] | 20%$^b$ |
| Example 26 | [structure: 3,4-F2-C6H3-CH=N-O-C(=O)-(CH2)8-CH3] | 12%$^b$ |

TABLE 2-continued

| Sample | | $IC_{50}$ (μM)[a] |
|---|---|---|
| Example 27 | (structure: 3,4-difluorobenzaldehyde O-(4-nitrobenzoyl)oxime) | 17%[b] |

[a]Data indicate average values of two test results.
[b]Inhibition rate at 25 μM As shown in table 2, O-acyloxime derivatives according to the present invention have excellent inhibitory activity of Lp-PLA$_2$ enzyme. Additionally, another Yacyloxime derivatives according to the present invention (not shown in table 2) have showed IC$_{50}$ value of 0.1 μM~25 μM and also have showed excellent inhibitory activity.

Accordingly, O-acyloxime derivatives according to the present invention may effectively be used for prevention and treatment of cardiovascular disease caused by Lp-PLA$_2$, such as hyperlipidemia, coronary arterial heart disease, atherosclerosis, and myocardial infarction.

EXPERIMENTAL EXAMPLE 2

Acute Toxicity Test of Oral Administration to Mouse

The following tests were carried out to observe acute toxicity of O-acyloxime derivatives according to the present invention.

Specific pathogens free ICR mice of 4 weeks old (12 females and 12 males; 3 females and 3 males/dosage group) were raised in an animal chamber controlled with the temperature of 22±3° C., humidity of 55±10%, and illumination of 12L/12D cycle. The mice were acclimated for a week before the test. Feed for a test animal (CJ Corp., for mouse and rat) and water were supplied after sterilization and taken by the mice without any restriction.

Each 50 mg/ml solution of (E)-3,4-di-fluorobenzaldehyde O-benzoyloxime of Example 21 or (E)-2,3-di-fluorobenzaldehyde O-morpholine-4-carbonyloxime of Example 30 in 0.5% Tween 80 was prepared. The amount of 0.04 ml (100 mg/kg), 0.2 ml (500 mg/kg), and 0.4 ml (1,000 mg/kg) per mouse weight of 20 g was dosed individually to the mice by oral administration. The samples were dosed only one time, and adverse effect and mortality were observed during 7 days after the dosing as follows. That is, changes of general symptoms and mortality were observed at 1 hour, 4 hours, 8 hours, and 12 hours after the administration, and one or more times in every morning and afternoon from the second day to the seventh day since the dosing day.

Additionally, on seventh day after the administration, the animals were sacrificed and dissected to examine internal organs with naked eye. Weight loss due to (E)-3,4-di-fluorobenzaldehyde O-benzoyloxime or (E)-2,3-di-fluorobenzaldehyde O-morpholine-4-carbonyloxime was observed by measuring weight changes at the intervals of 1 day since the dosage.

According to the test result, no observable toxicity was found in all the mice treated with the test material, and no dead mouse was found. Additionally, no toxicity was observed in terms of weight change, blood test, biochemical test of blood, and necropsy finding.

Accordingly, (E)-3,4-di-fluorobenzaldehyde O-benzoyloxime and (E)-2,3-di-fluorobenzaldehyde O-morpholine-4-carbonyloxime according to the present invention did not show any toxicity to all the mice up to the dosage of 1,000 mg/kg. Therefore, it was identified that the compounds are safe materials having the lethal dose 50(LD$_{50}$) by oral administration of at least more than 1,000 mg/kg.

Examples of pharmaceutical compositions containing the compounds according to the present invention are described as follows.

FORMULATION EXAMPLE 1

Pharmaceutical Formulation

| 1. Preparation of powder | |
|---|---|
| O-acyloxime derivative of Formula 1: | 2 g |
| Lactose: | 1 g |

A powder was prepared by mixing the above components and filling them into an airtight bag.

| 2. Preparation of Tablet | |
|---|---|
| O-acyloxime derivative of Formula 1: | 100 mg |
| Corn starch: | 100 mg |
| Lactose: | 100 mg |
| Magnesium stearate: | 2 mg |

A tablet was prepared by mixing the above components and tabletting them with a preparation method of a conventional tablet.

| 3. Preparation of Capsule | |
|---|---|
| O-acyloxime derivative of Formula 1: | 100 mg |
| Corn starch: | 100 mg |
| Lactose: | 100 mg |
| Magnesium stearate | 2 mg |

A capsule was prepared by mixing the above components and filling them into a gelatin capsule with a preparation method of a conventional capsule.

| 4. Preparation of Injection Solution | |
|---|---|
| O-acyloxime derivative of Chemical Formula 1: | 10 μg/ml, |
| Diluted hydrochloric acid BP: | added until reaching pH 3.5, |
| Sodium chloride BP for injection: | max. 1 ml. |

After dissolving O-acyloxime derivative of Formula 1 in sodium chloride BP for injection having a proper volume, pH of the formed solution was controlled to pH 3.5 with diluted hydrochloric acid BP. The volume of the solution was controlled with sodium chloride BP for injection, and then sufficiently mixed. After filling the solution into a 5 ml Type I ample made of transparent glass, the ample was sealed by melting the upper empty part of the ample, and sterilized for more than 15 minutes at 120° C. in an autoclave.

O-acyloxime derivatives according to the present invention have excellent inhibitory effect on Lp-$PLA_2$, and may thereby be effectively used for prevention and treatment of cardiovascular disease caused by Lp-$PLA_2$ such as hyperlipidemia, coronary arterial heart disease, atherosclerosis, and myocardial infarction.

While this invention has been described in connection with what is presently considered to be practical example embodiments, it should be understood that the invention is not limited to the disclosed embodiments, but, on the contrary, is intended to cover various modifications and equivalent arrangements included within the spirit and scope of the appended claims.

What is claimed is:

1. A compound of O-acyloxim, wherein the compound is selected from the group consisting of:
   7) (E)-4-fluorobenzaldehyde O-benzoyloxime,
   8) (E)-4-fluorobenzaldehyde O-4-fluorobenzoyloxime,
   21) (E)-3,4-di-fluorobenzaldehyde O-benzoyloxime,
   23) (E)-3,4-di-fluorobenzaldehyde O-4-fluorobenzoyloxime,
   27) (E)-3,4-di-fluorobenzaldehyde O-(4-nitro)benzoyloxime,
   28) (E)-3,4-di-fluorobenzaldehyde O-3,4-difluorobenzoyloxime,
   29) (E)-2,3-di-fluorobenzaldehyde O-benzoyloxime,
   31) (E)-2,4-di-fluorobenzaldehyde O-benzoyloxime,
   33) (E)-2,4-di-fluorobenzaldehyde O-4-fluorobenzoyloxime,
   34) (E)-2,6-di-fluorobenzaldehyde O-benzoyloxime, and
   36) (E)-3,5-di-fluorobenzaldehyde O-benzoyloxime.

2. A method for preparing a compound of O-acyloxime of claim 1 comprising:
   1) reacting a compound 2 with hydroxyamine in the presence of base to form a compound 3; and
   2) reacting the compound 3 prepared in the step 1) with acylchloride to form a compound 1,
   wherein,
   said compound 2 has a structure of

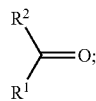

said compound 3 has a structure of

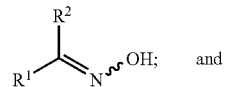

Said compound 1 is selected from the group consisting of:
   7) (E)-4-fluorobenzaldehyde O-benzoyloxime,
   8) (E)-4-fluorobenzaldehyde O-4-fluorobenzoyloxime,
   21) (E)-3,4-di-fluorobenzaldehyde O-benzoyloxime,
   23) (E)-3,4-di-fluorobenzaldehyde O-4-fluorobenzoyloxime,
   27) (E)-3,4-di-fluorobenzaldehyde O-(4-nitro)benzoyloxime,
   28) (E)-3,4-di-fluorobenzaldehyde O-3,4-difluorobenzoyloxime,
   29) (E)-2,3-di-fluorobenzaldehyde O-benzoyloxime,
   31) (E)-2,4-di-fluorobenzaldehyde O-benzoyloxime,
   33) (E)-2,4-di-fluorobenzaldehyde O-4-fluorobenzoyloxime,
   34) (E)-2,6-di-fluorobenzaldehyde O-benzoyloxime, and
   36) (E)-3,5-di-fluorobenzaldehyde O-benzoyloxime
   wherein,
   $R^1$ is phenyl, (3,5-di-t-butyl)-4-methoxyphenyl, 4-fluorophenyl, 3,5-difluorophenyl, 3,4-difluorophenyl, 2,6-difluorophenyl, 2,5-difluorophenyl, 2,4-difluorophenyl, or 2,3-difluorophenyl; and
   $R^2$ is hydrogen.

3. A pharmaceutical composition for treatment of cardiovascular disease wherein the cardiovascular disease is selected from the group consisting of hyperlipidemia, coronary arterial heart disease, atherosclerosis, and myocardial infarction comprising the compound of claim 1 and pharmaceutically acceptable salts thereof.

4. A Lp-$PLA_2$ inhibitor comprising the compound of claim 1 and pharmaceutically acceptable salts thereof.

5. A method for treating cardiovascular disease in a mammal wherein the cardiovascular disease is selected from the group consisting of hyperlipidemia, coronary arterial heart disease, atherosclerosis, and myocardial infarction comprising administering a therapeutically effective amount of the compound of claim 1 or pharmaceutically acceptable salt thereof, to the mammal.

6. A method for inhibiting A Lp-$PLA_2$ in a mammal comprising administering a therapeutically effective amount of the compound of claim 1 or pharmaceutically acceptable salt thereof, to the mammal.

7. A compound of O-acyloxime derivatives selected from the group consisting of:
   7) (E)-4-fluorobenzaldehyde O-benzoyloxime,
   21) (E)-3,4-di-fluorobenzaldehyde O-benzoyloxime, and
   27) (E)-3,4-di-fluorobenzaldehyde O-(4-nitro)benzoyloxime.

* * * * *